United States Patent
Ansorge et al.

(10) Patent No.: US 10,959,833 B2
(45) Date of Patent: Mar. 30, 2021

(54) IMPLANTABLE PROSTHESIS HAVING ACELLULAR TISSUE ATTACHMENTS

(71) Applicant: LifeCell Corporation, Branchburg, NJ (US)

(72) Inventors: Heather Ansorge, New Hope, PA (US); Lawrence Lapitan, Jersey City, NJ (US); Mark Hayzlett, Flemington, NJ (US); Nimesh Kabaria, Somerset, NJ (US); Raymond Hull, Hampton, NJ (US); Wenquan Sun, Warrington, PA (US); Michael Taenzer, Hackettstown, NJ (US); Matthew Amato, Lawrenceville, NJ (US); Timothy Roock, Bordentown, NJ (US); Dennis Lee, Scotch Plains, NJ (US)

(73) Assignee: LifeCell Corporation, Madison, NJ (US)

( * ) Notice: Subject to any disclaimer, the term of this patent is extended or adjusted under 35 U.S.C. 154(b) by 198 days.

(21) Appl. No.: 16/049,089

(22) Filed: Jul. 30, 2018

(65) Prior Publication Data

US 2018/0333252 A1 Nov. 22, 2018

Related U.S. Application Data

(63) Continuation of application No. 14/406,263, filed as application No. PCT/US2013/046349 on Jun. 18, 2013, now Pat. No. 10,039,633.

(Continued)

(51) Int. Cl.
*A61F 2/12* (2006.01)
*A61B 90/00* (2016.01)
*A61F 2/00* (2006.01)

(52) U.S. Cl.
CPC .............. *A61F 2/12* (2013.01); *A61B 90/02* (2016.02); *A61F 2/0059* (2013.01); *A61F 2210/009* (2013.01); *A61F 2210/0076* (2013.01); *A61F 2220/005* (2013.01); *A61F 2220/0016* (2013.01); *A61F 2220/0025* (2013.01); *A61F 2220/0033* (2013.01); *A61F 2220/0075* (2013.01); *A61F 2220/0091* (2013.01);

(Continued)

(58) Field of Classification Search
CPC combination set(s) only.
See application file for complete search history.

(56) References Cited

U.S. PATENT DOCUMENTS

| 2,108,205 A | 2/1938 | Martin |
| 3,683,424 A | 8/1972 | Pangman |

(Continued)

FOREIGN PATENT DOCUMENTS

| CN | 1953657 A | 4/2007 |
| DE | 102006029605 A1 | 12/2007 |

(Continued)

OTHER PUBLICATIONS

Baxter, Intracapsular allogenic dermal grafts for breast implant-related problems. Plast Reconstr Surg. Nov. 2003;112(6):1692-6.

(Continued)

*Primary Examiner* — Yashita Sharma
(74) *Attorney, Agent, or Firm* — McCarter & English, LLP

(57) ABSTRACT

Improved prostheses comprising a tissue expander and a graft material are disclosed herein. Also disclosed are methods of making prostheses and methods of treatment using the prostheses.

9 Claims, 10 Drawing Sheets

Related U.S. Application Data

(60) Provisional application No. 61/662,840, filed on Jun. 21, 2012.

(52) U.S. Cl.
CPC ............. *A61F 2230/0004* (2013.01); *A61F 2230/0045* (2013.01); *A61F 2230/0086* (2013.01); *A61F 2230/0089* (2013.01); *A61F 2230/0093* (2013.01); *A61F 2250/0003* (2013.01); *A61F 2250/0024* (2013.01); *A61F 2250/0031* (2013.01); *A61F 2250/0051* (2013.01); *A61F 2250/0071* (2013.01)

(56) References Cited

U.S. PATENT DOCUMENTS

| | | |
|---|---|---|
| 4,298,998 A | 11/1981 | Naticy |
| 4,840,629 A | 6/1989 | Bustos |
| 4,936,858 A | 6/1990 | O'Keeffe |
| 4,984,585 A | 1/1991 | Austad |
| 5,066,303 A | 11/1991 | Bark et al. |
| 5,352,307 A | 10/1994 | Wild |
| 5,356,429 A | 10/1994 | Seare |
| 5,447,535 A | 9/1995 | Muller |
| 5,584,884 A | 12/1996 | Pignataro |
| 5,658,328 A | 8/1997 | Johnson et al. |
| 5,658,330 A | 8/1997 | Carlisle et al. |
| 5,676,161 A | 10/1997 | Breiner |
| 5,713,959 A | 2/1998 | Bartlett et al. |
| 5,733,337 A | 3/1998 | Carr, Jr. et al. |
| 5,755,791 A | 5/1998 | Whitson et al. |
| 5,954,767 A | 9/1999 | Pajotin et al. |
| 5,968,096 A | 10/1999 | Whitson et al. |
| 5,997,575 A | 12/1999 | Whitson et al. |
| 6,051,648 A | 4/2000 | Rhee et al. |
| 6,099,566 A | 8/2000 | Vonderharr et al. |
| 6,203,570 B1 | 3/2001 | Baeke |
| 6,210,439 B1 | 4/2001 | Firmin et al. |
| 6,368,541 B1 | 4/2002 | Pajotin et al. |
| 6,638,308 B2 | 10/2003 | Corbitt, Jr. et al. |
| 6,666,892 B2 | 12/2003 | Hiles et al. |
| 6,723,133 B1 | 4/2004 | Pajotin |
| 6,736,823 B2 | 5/2004 | Darois et al. |
| 6,736,854 B2 | 5/2004 | Vadurro et al. |
| 6,740,122 B1 | 5/2004 | Pajotin |
| 6,777,231 B1 | 8/2004 | Katz et al. |
| 6,802,861 B1 | 10/2004 | Hamas |
| 7,011,688 B2 | 3/2006 | Gryska et al. |
| 7,081,135 B2 | 7/2006 | Smith et al. |
| 7,470,537 B2 | 12/2008 | Hedrick et al. |
| 7,476,249 B2 | 1/2009 | Frank |
| 7,699,895 B2 | 4/2010 | Hiles et al. |
| 7,875,074 B2 | 1/2011 | Chen et al. |
| 8,007,531 B2 | 8/2011 | Frank |
| 8,128,708 B2 | 3/2012 | Hiles et al. |
| 8,192,486 B2 | 6/2012 | Glicksman |
| 8,313,527 B2 | 11/2012 | Powell et al. |
| 8,383,092 B2 | 2/2013 | Lee et al. |
| 8,685,296 B2 | 4/2014 | Liu et al. |
| 8,858,647 B2 | 10/2014 | Markman |
| 8,876,899 B2 | 11/2014 | Maxwell |
| 8,986,377 B2 | 3/2015 | Richter et al. |
| 9,549,812 B2 | 1/2017 | Shetty et al. |
| 10,004,590 B2 | 6/2018 | Shetty et al. |
| 2001/0041936 A1 | 11/2001 | Corbitt et al. |
| 2002/0103542 A1 | 8/2002 | Bilbo |
| 2003/0036803 A1 | 2/2003 | McGhan |
| 2003/0130747 A1 | 7/2003 | Abraham et al. |
| 2003/0212461 A1 | 11/2003 | Vadurro et al. |
| 2003/0212462 A1 | 11/2003 | Gryska et al. |
| 2003/0225355 A1 | 12/2003 | Butler |
| 2004/0049269 A1 | 3/2004 | Corbitt et al. |
| 2004/0260315 A1 | 12/2004 | Dell et al. |
| 2005/0021141 A1 | 1/2005 | Bleyer et al. |
| 2005/0165425 A1 | 7/2005 | Croce et al. |
| 2005/0187624 A1 | 8/2005 | Corbitt |
| 2005/0250977 A1 | 11/2005 | Montpetit et al. |
| 2005/0260176 A1 | 11/2005 | Ayares et al. |
| 2006/0030939 A1 | 2/2006 | Frank |
| 2006/0167338 A1 | 7/2006 | Shfaram |
| 2006/0206189 A1 | 9/2006 | Furst et al. |
| 2007/0088299 A1 | 4/2007 | Ayre |
| 2007/0088434 A1 | 4/2007 | Frank |
| 2007/0116678 A1 | 5/2007 | Sung et al. |
| 2007/0250177 A1 | 10/2007 | Bilbo |
| 2008/0027273 A1 | 1/2008 | Gutterman |
| 2008/0082113 A1 | 4/2008 | Bishop et al. |
| 2008/0097601 A1 | 4/2008 | Codori-Hurff et al. |
| 2008/0108134 A1 | 5/2008 | Murphy et al. |
| 2008/0167729 A1 | 7/2008 | Nelson et al. |
| 2008/0241212 A1 | 10/2008 | Moses et al. |
| 2008/0260853 A1 | 10/2008 | Firestone |
| 2008/0281418 A1 | 11/2008 | Firestone |
| 2008/0281419 A1 | 11/2008 | Matheny et al. |
| 2009/0024227 A1 | 1/2009 | Lesh |
| 2009/0024228 A1 | 1/2009 | Lesh |
| 2009/0082864 A1 | 3/2009 | Chen et al. |
| 2009/0125107 A1 | 5/2009 | Maxwell |
| 2009/0198332 A1 | 8/2009 | Becker |
| 2009/0216338 A1 | 8/2009 | Gingras et al. |
| 2009/0240342 A1 | 9/2009 | Lindh, Sr. et al. |
| 2010/0010627 A1 | 1/2010 | Matheny |
| 2010/0023029 A1 | 1/2010 | Young |
| 2010/0028396 A1 | 2/2010 | Ward et al. |
| 2010/0191330 A1 | 7/2010 | Lauryssen et al. |
| 2010/0217388 A1 | 8/2010 | Cohen et al. |
| 2011/0009960 A1 | 1/2011 | Altman et al. |
| 2011/0022171 A1 | 1/2011 | Richter et al. |
| 2011/0035004 A1 | 2/2011 | Maxwell |
| 2011/0151011 A1 | 6/2011 | Flynn |
| 2011/0153017 A1 | 6/2011 | McClellan |
| 2011/0293666 A1 | 12/2011 | Wang et al. |
| 2011/0293667 A1 | 12/2011 | Baksh et al. |
| 2012/0052040 A1 | 3/2012 | Hunter et al. |
| 2012/0158134 A1 | 6/2012 | Codori-Hurff et al. |
| 2012/0255047 A1 | 10/2012 | Phelps et al. |
| 2012/0283826 A1 | 11/2012 | Moses et al. |
| 2013/0053956 A1 | 2/2013 | Powell et al. |
| 2013/0224260 A1 | 8/2013 | Ward et al. |
| 2014/0039617 A1 | 2/2014 | Maxwell |
| 2014/0257481 A1 | 9/2014 | Brooks et al. |
| 2014/0257482 A1 | 9/2014 | Ward et al. |
| 2015/0012089 A1 | 1/2015 | Shetty et al. |
| 2015/0150674 A1 | 6/2015 | Ansorge et al. |
| 2015/0157451 A1 | 6/2015 | Bowley et al. |
| 2015/0313708 A1 | 11/2015 | Mayo Martin |
| 2015/0359622 A1 | 12/2015 | Matheny |
| 2015/0359933 A1 | 12/2015 | Matheny |
| 2017/0007394 A1 | 1/2017 | Shetty et al. |
| 2018/0280132 A1 | 10/2018 | Shetty et al. |

FOREIGN PATENT DOCUMENTS

| | | |
|---|---|---|
| EP | 0338701 A2 | 10/1989 |
| FR | 2682284 A1 | 4/1993 |
| FR | 5746298 A1 | 9/1997 |
| JP | H10-158906 | 6/1998 |
| JP | 2005-536228 A | 12/2005 |
| WO | 2003/084410 | 10/2003 |
| WO | 2003/084410 A1 | 10/2003 |
| WO | 2004/096098 A1 | 11/2004 |
| WO | 2005/089411 A2 | 9/2005 |
| WO | 2006/115892 | 11/2006 |
| WO | 2006/115892 A2 | 11/2006 |
| WO | 2006/135998 A2 | 12/2006 |
| WO | 2007/004214 A2 | 1/2007 |
| WO | 2008/016919 A2 | 2/2008 |
| WO | 2008/121816 A2 | 10/2008 |
| WO | 2009/001293 A1 | 12/2008 |
| WO | 2009/065013 A1 | 5/2009 |

(56) References Cited

FOREIGN PATENT DOCUMENTS

WO    2009/114052 A2    9/2009
WO    2013/106556 A2    7/2013

OTHER PUBLICATIONS

Bindingnavele et al., Use of acellular cadaveric dermis and tissue expansion in postmastectomy breast reconstruction. J Plast Reconstr Aesthet Surg. 2007;60(11):1214-8.
Breuing et al., Immediate bilateral breast reconstruction with implants and inferolateral AlloDerm slings. Ann Plast Surg. Sep. 2005;55(3):232-9.
Breuing et al., Inferolateral AlloDerm hammock for implant coverage in breast reconstruction. Ann Plast Surg. Sep. 2007;59(3):250-5.
Colwell et al., Improving shape and symmetry in mastopexy with autologous or cadaveric dermal slings. Ann Plast Surg. Aug. 2008;61(2):138-42.
Darcy a technique for preparing meshed skin grafts with planned expansion ratios. Br J Plast Surg. Jan. 2003;56(1):77-9.
Duncan, Correction of implant rippling using allograft dermis. Aesthet Surg J. Jan. 2001;21(1):81-4.
Gamboa-Bobadilla, Implant breast reconstruction using acellular dermal matrix. Ann Plast Surg. Jan. 2006;56(1):22-5.
Góes et al., The application of mesh support in periareolar breast surgery: clinical and mammographic evaluation. Aesthetic Plast Surg. Sep.-Oct. 2004;28(5):268-74.
Góes, Periareolar Mammaplasty with Mixed Mesh Support: The Double Skin Technique. Operative Techniques in Plastic and Reconstructive Surgery. Aug. 1993;3(3):199-206.
Góes, Periareolar mammaplasty: double skin technique with application of polyglactine or mixed mesh. Plast Reconstr Surg. Apr. 1996;97(5):959-68.
Góes, Periareolar Mammaplasty: Double Skin Technique with Application of Polygractine 910 Mesh. Rev. Soc. Bras. Cir. Plast. Estet. Reconstr. Jan./Dec. 1992;7(1,2,3):1-5.
Góes, Periareolar Mastopexy and Reduction with Mesh Support, Double Skin Technique. Surgery of the Breast: Principles and Art Scott L. Spear (Ed.), Lippincott-Raven Publishers, Philadelphia. Chapter 51, pp. 697-708 (1998).
Góes, Periareolar Mastopexy: Double Skin Techique with Mess Support Aesthetic Surgery Journal. Mar.-Apr. 2003;23:129-135.
Pope, Mesh Skin Grafting. Veterinary Clinics of North America: Small Animal Practice. Jan. 1990;20(1):177-187.
Salzberg, Nonexpansive immediate breast reconstruction using human acellular tissue matrix graft (AlloDerm). Ann Plast Surg. Jul. 2006;57(1):1-5.
Topol et al., Immediate single-stage breast reconstruction using implants and human acellular dermal tissue matrix with adjustment of the lower pole of the breast to reduce unwanted lift. Ann Plast Surg. Nov. 2008;61(5):494-9.
Zienowicz et al., Implant-based breast reconstruction with allograft. Plast Reconstr Surg. Aug. 2007;120(2):373-81.
International Search Report and Written Opinion for Application No. PCT/US2010/042575, dated Jan. 14, 2011.
Goes; "Periareolar Mastopexy: Double Skin Techique with Mess Support;" Aesthetic Surgery Journal (Mar./Apr. 2003).
Goes; "Periareolar Mastopexy and Reduction with Mesh Support, Double Skin Technique;" Surgery of the Breast: Principles and Art; 697 (1998).
Goes; "Periareolar mammaplasty: Double Skin Technique with Application of Polyglactine or Mixed Mesh;" Plastic and Reconstructive Surgery (Apr. 1996).
Goes; "Periareolar Mammaplasty: Double Skin Technique with Appliction of Polygractine 910 Mesh;" Rev. Soc. Bras. Cir. Plast. Estet. Reconstr.; 7(1,2,3)(1992).
Baxter; "Intracapsular Allogenic Dermal Grafts for Breaast Implant-Related Problems": Plast. R3econstr. Surg.; 112(6):1692-1696 (2003).
Breuing et al.; "Inferolateral AlloDerm Hammock for Implant Coverage in Breast Cadaveric Dermal Slings"; Annals of Plastic Surgery; 59(3):250-255 (2007).
Salzberg; "Nonexpansive Immediate Breast Reconstruction Using Human Acellular Tissue Matrix Graft (AloDerm)"; Annals of Plastic Surgery; 57(1):1-5 (2006).
Zienowicz et al.; "Implant-based Breast Reconstruction With Allograft"; Plast. Reconstr. Surg.; 120:373-374 (2007).
International Search Report and Written Opinion for Application No. PCT/US2013/046349, dated Oct. 2, 2013.

IMPLANTABLE PROSTHESIS HAVING ACELLULAR TISSUE ATTACHMENTS

Disclosed herein are implantable prostheses, such as breast implants and tissue expanders, for use in various surgical procedures.

Implantable prostheses, such as breast implants and tissue expanders, are used in a wide range of surgical procedures. For example, the prostheses can be used for breast augmentation, reconstruction, and/or revision. But, even though the implants and tissue expanders used in these surgical procedures are biocompatible and non-reactive, post-surgical complications can still result from their use, such as capsular contracture, scar formation, implant displacement, rippling, and palpability of implants. Research has focused on surgical techniques and modified implant characteristics, which may result in reduced incidence of complications. One approach that surgeons use to improve outcomes, reduce the risk of complications, and/or provide improved revisions is to use graft materials, such as acellular dermal tissue matrices like ALLODERM® or STRATTICE™ (LIFECELL CORPORATION, Branchburg, N.J.), along with the tissue expanders or breast implants.

The current standard of care during surgical breast procedures involves separately attaching a graft material to a patient and then placing a prosthesis in the patient. In one procedure the surgeon first attaches the graft material to the infra mammary fold (IMF) and the pectoralis major muscle in order to create a submuscular pocket or flap. Next, the surgeon places the breast implant or tissue expander inside the pocket. The process of attaching the graft material to the native tissue can require a substantial amount of time and involve the use of sutures or other devices to anchor the graft material to the native tissue. The current process can also lead to inconsistent results, as inexperienced surgeons may not use graft materials of optimal shape, or may incorrectly position the implant or tissue expander relative to the graft material.

Accordingly, there is a need for improved prostheses comprising tissue expanders, methods of making these prostheses, and methods of treatment using such prostheses.

In various embodiments, an implantable prosthesis is disclosed herein, comprising a tissue expander and one or more samples of graft material, wherein the tissue expander is attached to the one or more samples of graft material in a manner that allows the tissue expander and the one or more samples of graft material to be implanted in a patient as a unitary prosthesis, and wherein the implant or tissue expander is attached to the one or more samples of graft material in a manner that will allow the tissue expander and the graft material to be easily separated naturally or through surgical intervention after a period of time following implantation. In some embodiments, the prosthesis comprises molded grooves, slots, channels or other shallow cavity spaces that secure the graft material to the tissue expander. In certain embodiments, the prosthesis comprises a biocompatible flap or pocket on the surface of the tissue expander that secures the graft material to the tissue expander.

In some embodiments, the prosthesis comprises one or more fixation tacks comprising one or more thin strands of biocompatible material and one or more barbs that secure the graft material to the tissue expander. In some embodiments, the prosthesis comprises one or more zip ties that secure the graft material to the tissue expander. In some embodiments, the one or more samples of graft material comprise one or more holes, slits, or apertures through which the one or more fixation tacks or zip ties are passed to secure the graft material to the tissue expander.

In certain embodiments, the prosthesis comprises a belt that secures the graft material to the tissue expander. In some embodiments, the belt comprises slots, and the graft material is shaped to provide tabs or other shapes that will fit within the slots on the belt, thereby securing the graft material to the belt.

In some embodiments, the prosthesis comprises attachment points, wherein the attachment points comprise a dissolvable hard material, are attached to an exterior surface of the tissue expander or underneath the exterior surface of the tissue expander, and are in the form of dissolvable tabs, clips, balls, or buttons. In some embodiments, the one or more samples of graft material comprise one or more holes, slits, or apertures through which the attachment points are passed to secure the graft material to the tissue expander. In some embodiments, the attachment points dissolve or otherwise detach after a period of time following implantation, thereby releasing the graft material.

In certain embodiments, a prosthesis further comprises one or more magnets that secure the graft material to the tissue expander. In some embodiments, the prosthesis also comprises a biocompatible flap and two or more magnets, wherein at least one magnet is secured to a surface of the tissue expander and at least one magnet is secured to the flap on the tissue expander, and wherein the graft material is secured between the two magnets.

In various embodiments, the graft material comprises an acellular tissue matrix. For example, the acellular tissue matrix can comprise an adipose acellular tissue matrix that has been treated to produce a three-dimensional porous or sponge-like material.

In various embodiments, a method of making an implantable prosthesis is disclosed, comprising attaching one or more samples of graft material to a tissue expander comprising at least one of: one or more molded grooves, slots, channels or other shallow cavity spaces; a flap or pocket; one or more fixation tacks; one or more zip ties; a belt; one or more attachment points; or one or more magnets. In some embodiments, the graft material is secured to the tissue expander by interacting with the one or more molded grooves, slots, channels or other shallow cavity spaces; flap or pocket; belt; one or more fixation tacks; one or more zip ties; one or more attachment points; or one or more magnets. In some embodiments, after attaching the graft material to the shell of the tissue expander, the prosthesis is heat cured. In some embodiments, the prosthesis is heat cured at a temperature of about 30° C. or less, or at a temperature of between about 70° C. and 120° C.

Furthermore, in various embodiments, methods of treatment using the disclosed prostheses are provided herein, comprising implanting a prosthesis into a tissue and then removing the tissue expander after a predetermined length of time while leaving the one or more samples of graft material at the implant site. In some embodiments, the tissue expander separates from the graft material over time following implantation without requiring surgical intervention. In other embodiments, the tissue expander is manually separated from the graft material prior to removal of the tissue expander. In certain embodiments, a prosthesis as disclosed herein is implanted as part of a breast augmentation procedure.

DESCRIPTION OF CERTAIN EXEMPLARY EMBODIMENTS

Figure 1A:
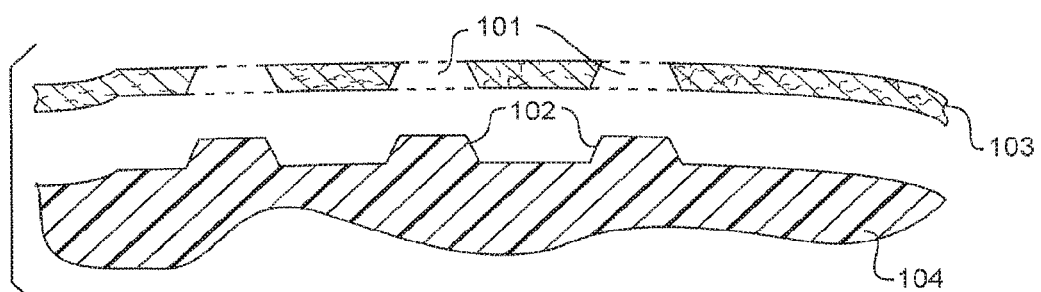
FIG. 1A illustrates a portion of a prosthesis, according to certain embodiments of the disclosure, comprising a tissue expander having a grooved surface and a graft material shaped to conform to the grooves.

Reference will now be made in detail to certain exemplary embodiments of the invention, certain examples of which are illustrated in the accompanying drawings.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Any range described herein will be understood to include the endpoints and all values between the endpoints. Also, terms such as "element" or "component" encompass both elements and components comprising one subunit and elements and components that comprise more than one subunit, unless specifically stated otherwise. Also, the use of the term "portion" may include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "graft material," as used herein, generally refers to a biocompatible material, or a combination of biocompatible materials, such as, for example, one or more samples of tissue, processed tissue, partially or completely decellularized tissue, and/or synthetic material that can be attached to a prosthesis, inserted into an implant site, and promote the migration and/or proliferation of native cells within the graft material.

The terms "breast implant" and "implant," as used herein, generally refer to medical devices that are implanted either under or within breast tissue or under the chest muscle for breast augmentation or reconstruction. Such implants can include saline filled or silicone gel implants, or other implants that provide volume for breast augmentation. The terms "breast tissue expander," "tissue expander," and "expander," as used herein, generally refer to devices that are implanted under or within breast or other tissue or muscle, and which are expanded over time to stretch breast or other tissue and skin. The tissue expander can be made from any biocompatible and/or non-reactive material commonly used in implantable medical devices such as standard tissue expanders or breast implants. Unless otherwise indicated, different tissue expanders can be used interchangeably with the different graft materials and methods disclosed herein. Furthermore, the term "prosthesis" will be understood to include any implantable device disclosed herein that comprises a tissue expander component and one or more samples of graft material.

The term "resorbable biocompatible polymer," as used herein, refers to a polymer that can be dissolved or otherwise absorbed by the body over time following implantation and which does not elicit a substantial immune or inflammatory response following implantation. A substantial immune or inflammatory response includes any response that prevents or hinders the migration of native cells into the extracellular matrix of the graft material or prevents the partial or complete repopulation of the graft material with native cells. For example, the resorbable polymer can comprise aliphatic polyester polymers and copolymers and blends thereof, polymers of lactide or galactide or copolymers thereof, polysaccharides such as cellulose, oxidized polysaccharides, or other absorbable polymers. As used herein, the terms "native cells" and "native tissue" mean the cells and tissue present in the recipient tissue/organ prior to the implantation of a prosthesis, or the cells or tissue produced by the host animal after implantation The present disclosure relates to prostheses, methods of making prostheses, and methods of treatment using the prostheses. In various embodiments, the prostheses disclosed herein can be used with any surgical procedure where tissue expansion is desirable (e.g., to stretch tissue harvested for use in autologous skin grafts). As such, the implantable prostheses and methods discussed herein may be suitable for a wide range of surgical applications. In some embodiments, the prostheses and methods discussed herein may be suitable for various types of surgical breast procedures, such as, for example, aesthetic surgery associated with mastectomy or lumpectomy, breast reconstruction, breast augmentation, breast enhancement, mastopexy, and/or revisionary breast surgeries.

According to certain embodiments, a prosthesis is disclosed. The prosthesis can comprise a tissue expander and one or more samples of graft material, wherein the tissue expander is attached to the one or more samples of graft material in a manner that allows the tissue expander and the one or more samples of graft material to be implanted in a patient as a unitary prosthesis; and wherein the implant or tissue expander is attached to the one or more samples of graft material in a manner that will allow the tissue expander and the graft material to be easily separated after a period of time following implantation. The tissue expander can be made from any biocompatible and/or non-reactive material commonly used in implantable medical devices such as standard tissue expanders or breast implants.

In certain embodiments, the structure of the tissue expander, along with its attachment to a graft material such as an acellular tissue matrix, allows the tissue expander to be enlarged and subsequently removed after a certain period of time, without removing the graft material. Accordingly, the devices and methods of the present disclosure can be beneficial for reconstruction procedures that require removal of tissue expanders but where retention of a graft material would be desirous.

By providing a tissue expander and one or more samples of graft material as a unitary prosthesis, the implantable prostheses of the present disclosure can, in some embodiments, shorten procedure time, reduce the number of surgical sutures, staples and/or other attachment devices needed to secure the prostheses, and reduce the associated costs of surgery. In certain embodiments, the implantable prostheses can also improve surgical outcomes and improve consistency of results. In some embodiments, the implantable prostheses reduce the incidence of extrusion and/or capsular contraction, block or reduce inflammatory responses, and/or result in shorter expansion times.

In some embodiments, the tissue expanders can be implanted as unitary prostheses. In some embodiments, the implantable prostheses of the present disclosure can be constructed such that the tissue expander can easily separate from the graft material after implantation. In various embodiments, the graft material is attached to the tissue expander in such a way that the two will separate before the tissue expander is removed. In some embodiments, the tissue expander is designed to separate from the graft material after a period of time. In certain embodiments, the graft material is attached to the tissue expander in such a way that the graft material and tissue expander will separate without requiring surgical intervention. In other embodiments, the graft material is attached to the tissue expander in such a way that the two can be easily separated when the tissue expander is surgically removed, leaving the graft material at the implant site.

According to certain embodiments, a prosthesis is disclosed that comprises a tissue expander and one or more samples of graft material sized and/or shaped to conform to a portion of a surface of the tissue expander, wherein the one or more samples of graft material is attached to the tissue expander in such a way as to temporarily secure the graft material in place but to release the graft material from the tissue expander over time following implantation.

Figure 1B:
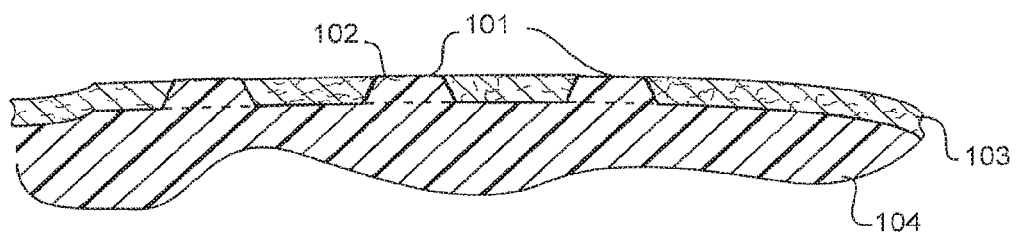
FIG. 1B shows the graft material secured to the grooves on the tissue expander.

For example, in some embodiments, a tissue expander may comprise molded grooves, slots, channels or other shallow cavity spaces on the surface of the expander. For instance, FIG. 1A illustrates a portion of a tissue expander having a surface 103 containing grooves 101. Graft material 104, optionally containing shaped components 102 that conform to the grooves 101 or other cavity spaces, can be placed within the cavity spaces in the tissue expander. In some embodiments, the graft material 104 is initially held in place by the edges of the cavity spaces in the tissue expander (FIG. 1B), which press against all or some of the graft material 104 and provide a frictional force to prevent the graft material 104 from migrating away from the expander. Over time, the graft material 104 can separate from the tissue expander. For example, the graft material 104 may naturally migrate away from the expander as the frictional force holding it in place lessens after implantation (e.g., due to the aqueous environment, due to the deformation of the expander or the graft material following implantation, and/or due to the natural flexibility of the grooves, slots, channels or other shallow cavity spaces). Alternatively, in some embodiments the graft material 104 may be released from the cavity spaces as the tissue expander is filled after implantation, thereby stretching the edges of the cavity space and removing the frictional force securing the graft material 104 to the expander.

Figure 2:
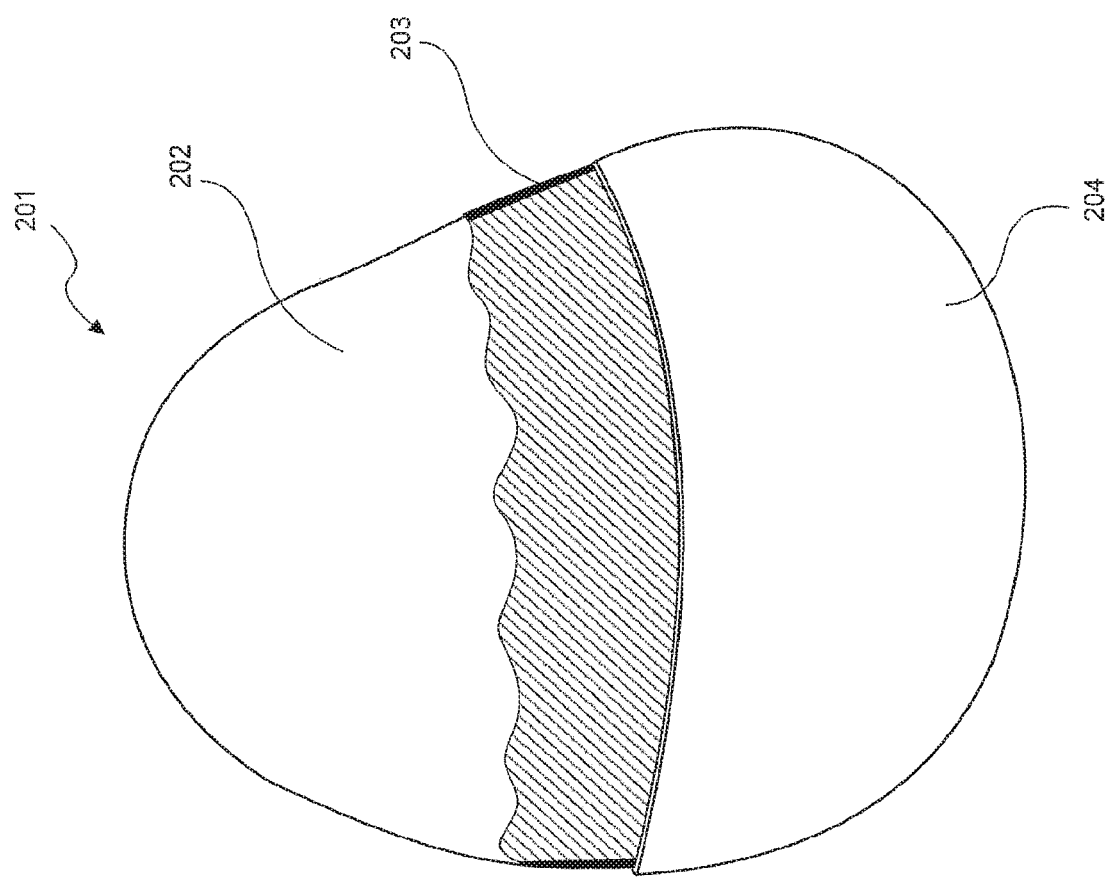
FIG. 2 illustrates a portion of a prosthesis, according to certain embodiments, comprising a tissue expander having a polymeric flap, wherein the flap serves to secure a graft material to the surface of the prosthesis.

In another example, a graft material can be secured to a tissue expander by a flap or pocket of biocompatible material on the surface of the tissue expander. In some embodiments, the flap or pocket is secured at one end but able to slide relative to the underlying surface of the tissue expander. For example, FIG. 2 illustrates a portion of a prosthesis 201 comprising a tissue expander 202 having a polymeric flap or pocket 204, wherein the flap or pocket 204 serves to secure a graft material 203 to the surface of the tissue expander 202. The flap or pocket 204 can comprise a biocompatible material (e.g., silicone). The graft material 203 can be placed in the flap or pocket 204, temporarily securing the graft material 203 to the expander 202. As the tissue expander 202 is filled, the flap or pocket 204 is retracted, releasing the graft material 203.

Figure 3:
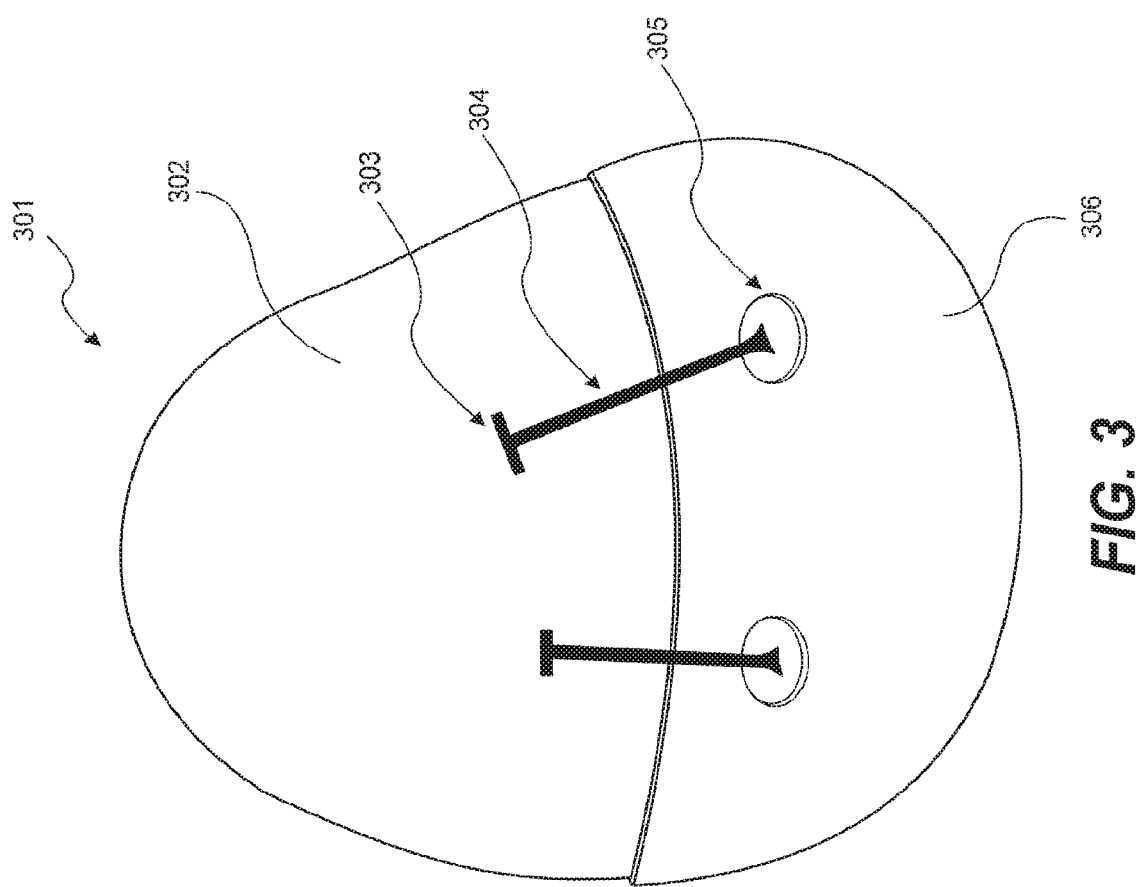
FIG. 3 illustrates a portion of a prosthesis, according to certain embodiments, comprising a tissue expander having two thin polymeric cords that can be passed through holes in a graft material and attached to the surface of the tissue expander using fixation tacks provided at the ends of the thin polymeric cords.

In yet another example, a graft material can be secured to a tissue expander using fixation tacks. For example, a tissue expander can comprise one or more thin cords or strands of biocompatible material (e.g., silicone). In some embodiments, the cords can have a branched structure, such as a T-tack structure. In certain embodiments, the ends of the cords can comprise tacks or other textured surfaces that can engage the surface of a tissue expander and/or a graft material. In some embodiments, a graft material comprising at least one hole is secured to the tissue expander by passing the one or more cords or strands through the at least one hole in the graft material. In certain embodiments, the tacks or textured surface on the end of the cord or strand is placed in contact with the tissue expander or graft material after being passed through the one or more holes on the graft material, anchoring the graft material to the expander. In some embodiments, the graft material comprises at least two holes, and the cords or strands are threaded through both holes, thereby anchoring the graft to the underlying expander. In various embodiments, filling the tissue expander exerts tension on the cords or strands, causing the tacks or other textured surfaces to release, thereby freeing the graft material from the tissue expander. In other embodiments, the cords or strands comprise a resorbable polymer (e.g., aliphatic polyester polymers, copolymers, blends thereof, polymers of lactide, galactide, or copolymers thereof, polysaccharides such as cellulose, and oxidized polysaccharides, or other absorbable polymers) that dissolves over time following implantation, thereby releasing the graft material. For example, FIG. 3 illustrates a portion of a prosthesis 301 comprising a tissue expander 302 having two thin polymeric cords 304 that pass through holes 305 in a graft material 306 and attach to the surface of the tissue expander 302 using fixation tacks 303.

Figure 4:
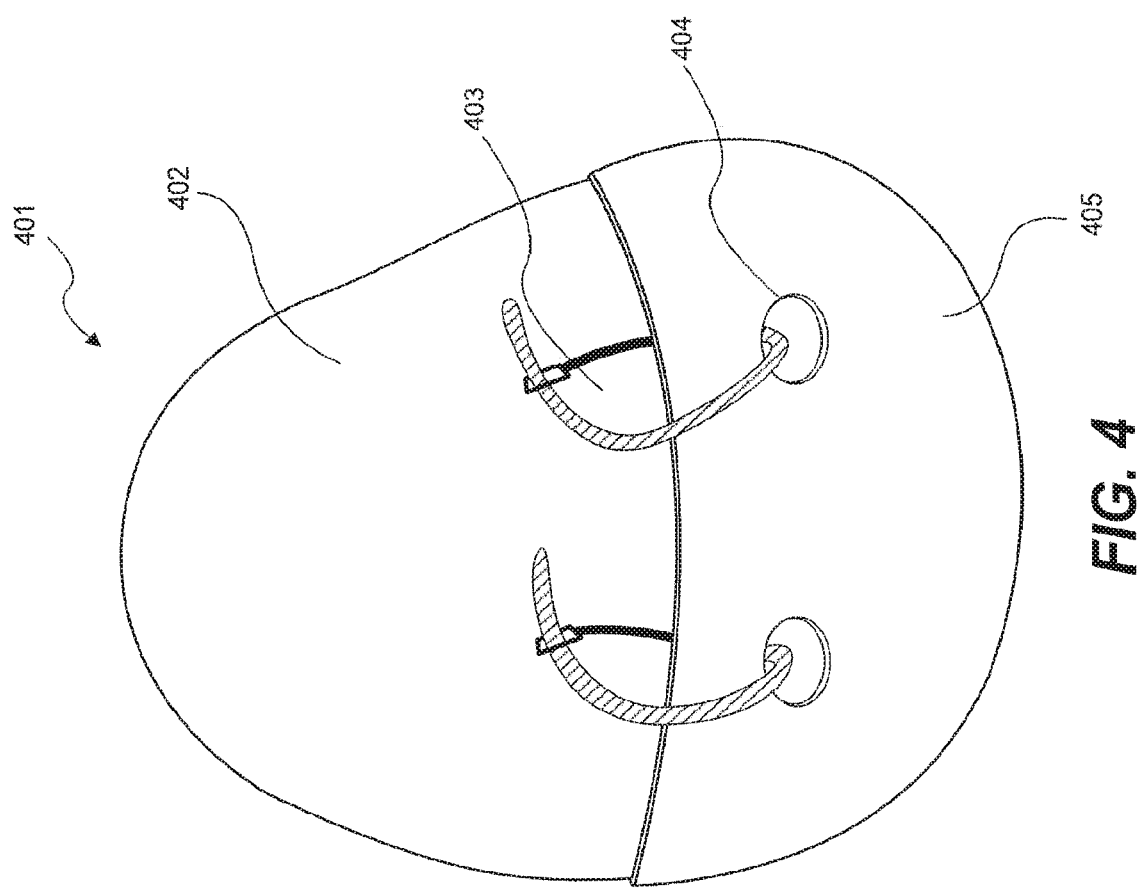
FIG. 4 illustrates a portion of a prosthesis, according to certain embodiments, comprising a tissue expander having two zip ties that can be passed through holes in a graft material and thereby secure the graft material to the tissue expander.

In still another example, a graft material can be secured to a tissue expander using zip ties. For example, a tissue expander comprising one or more attached zip ties can be prepared. The zip ties can comprise a biocompatible material (e.g., silicone). In some embodiments, the zip ties are passed through one or more holes in a graft material and then passed through the locking point in the zip tie, securing the graft material to the tissue expander. In some embodiments, the zip ties are manually released by the surgeon prior to surgical removal of the tissue expander. In another embodiment, the zip ties are prepared from a resorbable, biocompatible material that dissolves over time after exposure to the aqueous implant environment, thereby releasing the graft material. In certain embodiments, the resorbable polymer can comprise aliphatic polyester polymers, copolymers, blends thereof, polymers of lactide, galactide, or copolymers thereof, polysaccharides such as cellulose, and oxidized polysaccharides, or other absorbable polymers). For example, FIG. 4 illustrates a portion of a prosthesis 401 comprising a tissue expander 402 having two zip ties 403 that pass through holes 404 in a graft material 405 and secure the graft material 405 to the tissue expander 402.

Figure 5A:
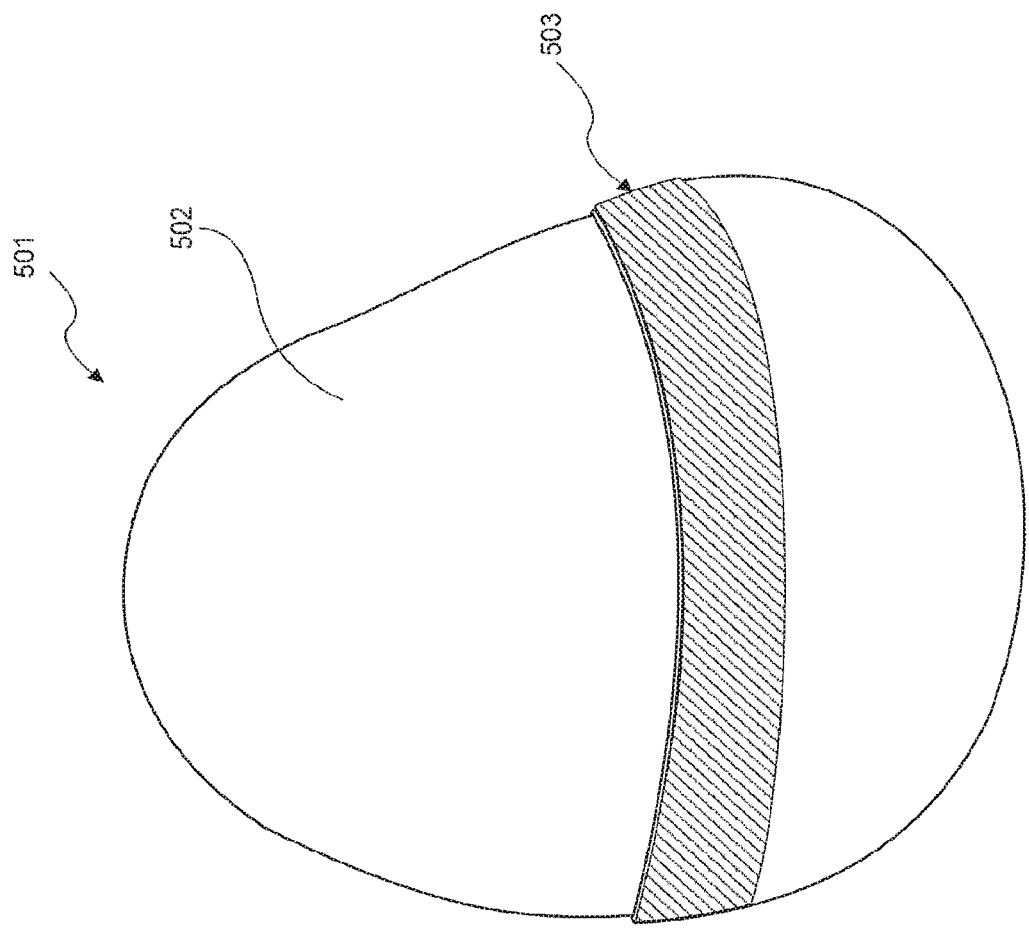
FIG. 5A illustrates a portion of a prosthesis, according to certain embodiments, comprising a tissue expander having a polymeric belt used to secure a graft material to the tissue expander.
Figure 5B:
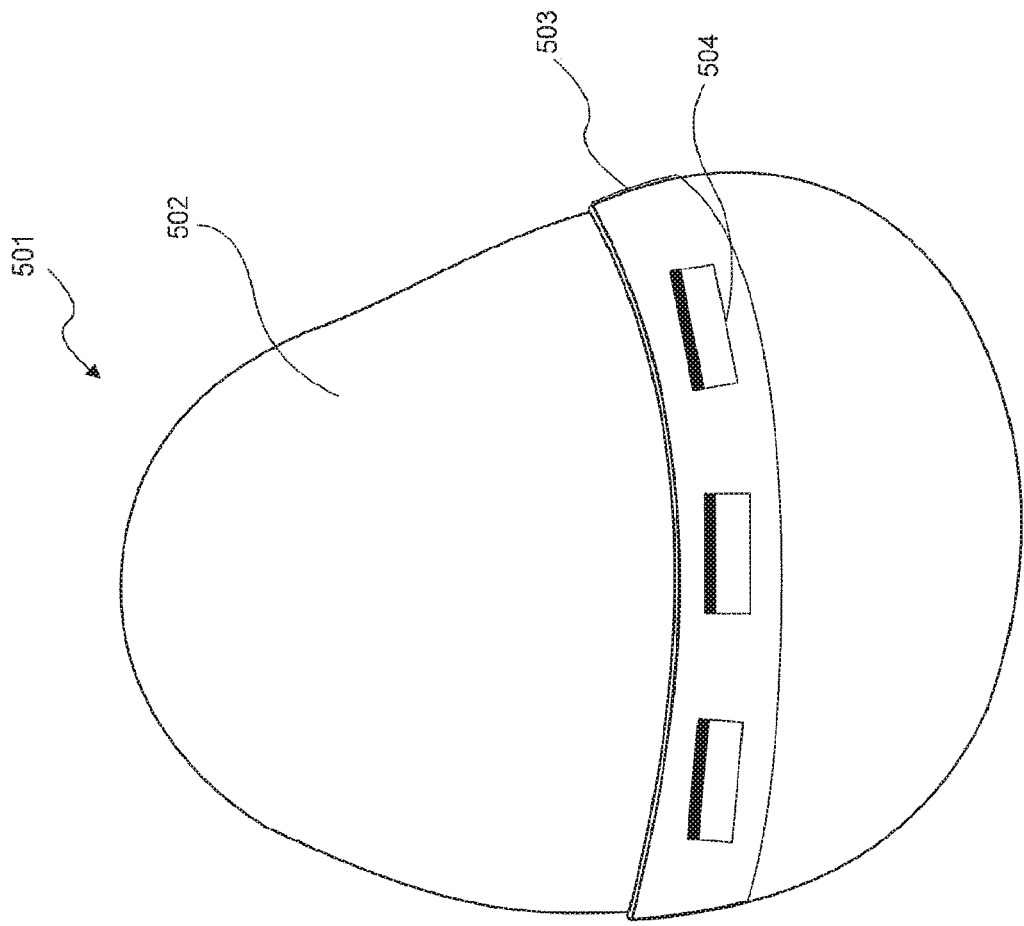
FIG. 5B illustrates a portion of a prosthesis, according to certain embodiments, comprising a tissue expander having a polymeric belt comprising slots used to secure a graft material to the tissue expander.
Figure 5C:
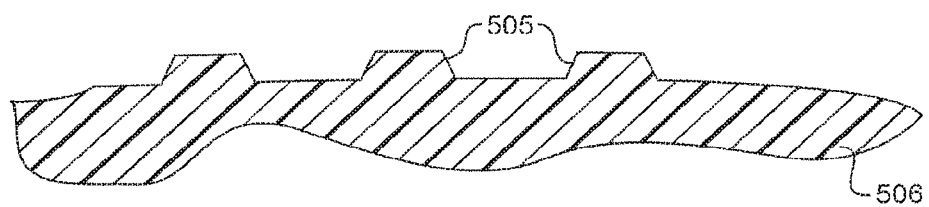
FIG. 5C illustrates a portion of a graft material, according to certain embodiments, shaped to have components that will fit into the slots in the belt shown in FIG. 5B.

In another example, a tissue expander can comprise a belt used to secure a graft material. For example, FIG. 5A illustrates a portion of a prosthesis 501 comprising a tissue expander 502 having a polymeric belt 503 used to secure a graft material to the tissue expander 502. In various embodiments, the belt 503 may comprise a biocompatible material (e.g., silicone). In some embodiments, the graft material can be inserted under the belt 503, securing the graft to the expander 502. In certain embodiments, the belt can comprise slots, and the graft material can be shaped to provide tabs or other shapes that will fit within the slots on the belt, thereby securing the graft material to the belt. For example, FIG. 5B illustrates a portion of a prosthesis 501 comprising a tissue expander 502 having a polymeric belt 503 comprising slots 504 used to secure a graft material to the tissue expander 502. In some embodiments, a graft material, such as the graft material 506 shown in FIG. 5C, is shaped to have components 505 that will fit into the slots 504 in the belt 503, thereby securing the graft material 506 to the tissue expander 502.

In some embodiments, as the tissue expander is filled, the belt that secures the graft to the expander is stretched, reducing the tension applied by the belt on the graft material, and thereby releasing the graft material from the tissue expander. In other embodiments, the graft material is manually released from the belt by the surgeon when the tissue expander is removed. In other embodiments, the belt comprises a resorbable polymer (e.g., aliphatic polyester polymers, copolymers, blends thereof, polymers of lactide, galactide, or copolymers thereof, polysaccharides such as cellulose, and oxidized polysaccharides, or other absorbable polymers) that dissolves over time following implantation, thereby releasing the graft material.

Figure 7A:
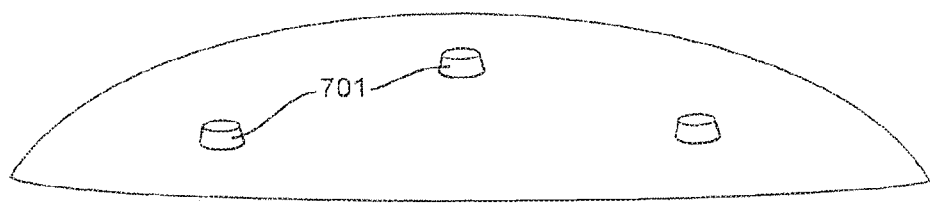
FIG. 7A-C illustrates portions of prostheses, according to certain embodiments, comprising tissue expanders having examples of three different types of attachment points for use in securing a graft material to the tissue expander.
Figure 7B:
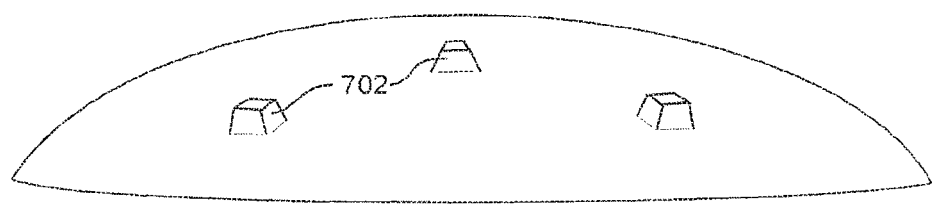
Figure 7C:
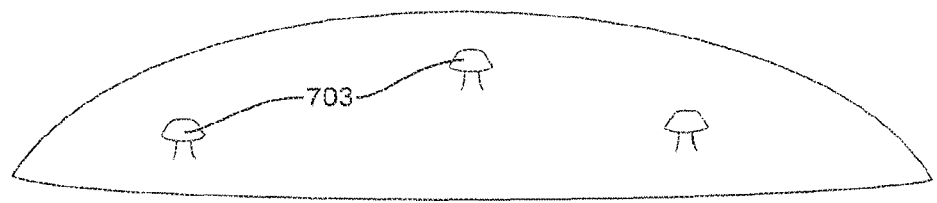
Figure 7D:
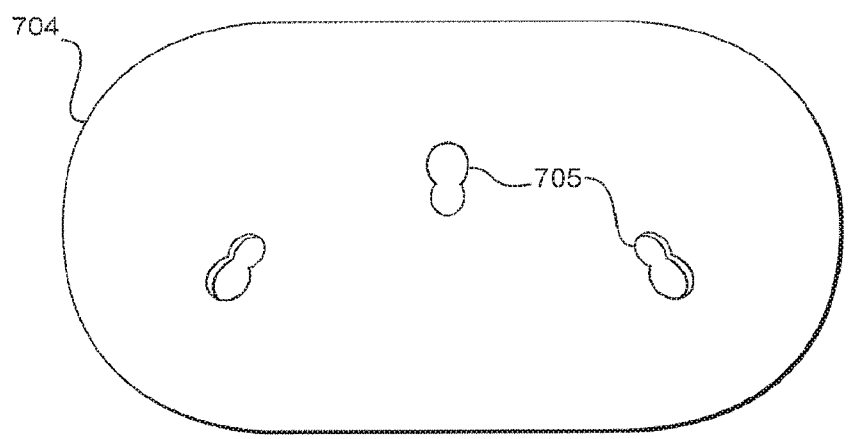
FIG. 7D illustrates a portion of a graft material, according to certain embodiments, having holes for use in securing the graft material to the tissue expanders shown in FIG. 7A-C.

In various embodiments, a tissue expander can comprise attachment points (e.g., clips, balls, buttons or tabs) on at least a portion of the outer surface. For example, FIG. 7A-C illustrates portions of tissue expanders having three different types of attachment points 701, 702, and 703 for use in securing a graft material to the tissue expander. The attachment points 701-703 can be used to secure the graft material to the expander, for example by folding over the edges of the graft material, or by pushing the attachment points 701-703 through holes, slits, or other perforations placed in the graft material, thereby securing the graft material in place. For example, FIG. 7D illustrates a portion of a graft material 704 having holes 705 through which the attachment points 701-703 can be passed to secure the graft material 704 to the tissue expander. The attachment points 701-703 can have any shapes suitable for securing a graft material, for example balls, cylinders, cylinders with widened heads, button, curved shapes, etc. Over time, the attachment points 701-703 are designed to dissolve, separate, detach, or otherwise release the graft material 704 from the tissue expander.

For example, in certain embodiments a hard material can be placed underneath the outer membrane of the tissue expander and press out through the membrane to create the attachment points. For example, a hard material in the shape of tabs, clips, balls, buttons, or other desired shapes can be affixed along the inner surface of the expander and bulge out through the membrane to create attachment points for the graft material. The hard material can be used to secure the graft material to the expander, for example by folding over the edges of the graft material, or by pushing through holes, slits, or other perforations placed in the graft material, thereby securing the graft material in place. In some embodiments, the hard material comprises a material that is soluble in aqueous solution. Over time, the saline or other aqueous solution in the tissue expander can dissolve the hard material, thereby releasing the graft material. Examples of suitable hard materials include, but are not limited to, polycaprolactone, polylactic acid, polygalacturonic acid, polymer polyglycolic-lactic acid, polyhydroxyalkanoates, polydioxanone, or any other similar polymers or biological materials known to degrade in vivo.

In another example, the attachment points can comprise a hard material attached to the external surface of a tissue expander. In some embodiments, the attachment points comprise tabs, clips, balls, buttons, or other desired shapes that secure the graft material to the expander, for example by folding over the edges of the graft material, or by pushing through holes, slits, or other perforations placed in the graft material, thereby securing the graft material in place. In some embodiments, the attachment points are designed to release when exposed to force as the tissue expander is filled. For example, filling the tissue expander can lift or stretch the tabs that hold a graft material against a tissue expander, bending the tabs away from the graft material and releasing the graft material from the expander. Similarly, in another example, filling the tissue expander can stretch the graft material secured to it, thereby transmitting a torsional force to the attachment points (e.g., the tabs, clips, balls, buttons, or other shapes) as the graft material pulls on them, resulting in the deformation or detachment of the attachment points and release of the graft material. In other embodiments, the attachment points may comprise a resorbable, biocompatible material that dissolves over time when exposed to the aqueous environment of the implant site, thereby releasing the graft material. For example, the resorbable material can comprise aliphatic polyester polymers, copolymers, blends thereof, polymers of lactide, galactide, or copolymers thereof, polysaccharides such as cellulose, and oxidized polysaccharides, or other absorbable polymers that dissolve over time following implantation, thereby releasing the graft material.

Figure 6:
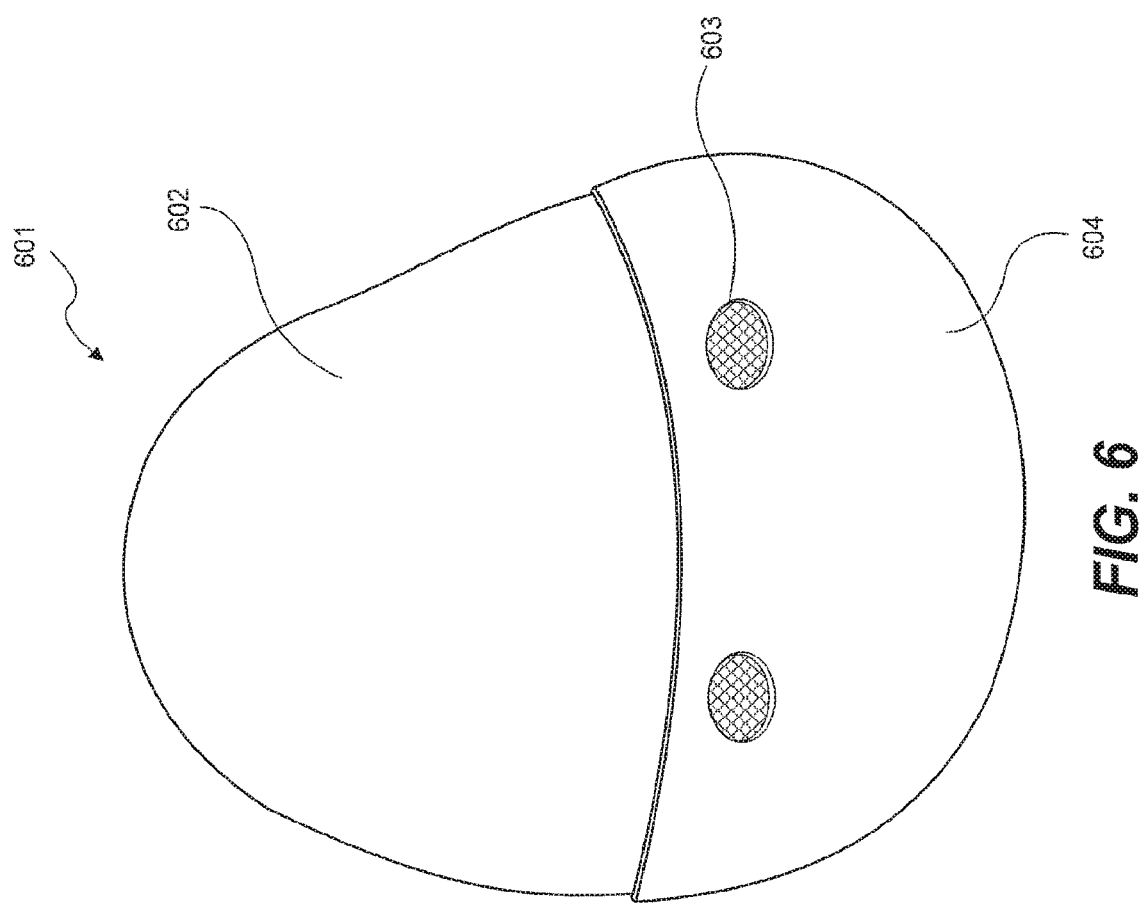
FIG. 6 illustrates a portion of a prosthesis, according to certain embodiments, comprising a tissue expander having a flap of biocompatible material and two magnets used to secure the open end of the flap to the tissue expander.

In various embodiments, a graft material can be secured to a tissue expander using one or more magnets. For example, FIG. 6 illustrates a portion of a prosthesis 601 comprising a tissue expander 602 having a flap 604 of biocompatible material and two magnets 603, with one portion of the magnet 603 secured to the inner surface of the tissue expander 602 and the other portion of the magnet 603 secured to the flap 604 of the tissue expander 602. In some embodiments, a graft material can be placed over the tissue expander 602 or over a portion of the tissue expander 602 comprising the at least one magnet 603. The flap 604 comprising at least one magnet 603 can be folded down over the graft material to interact with the magnet 603 on the inner surface of the tissue expander 602, thereby securing the graft material between the flap 604 and the tissue expander 602. In some embodiments the one or more magnets and the flap comprise biocompatible materials.

According to certain embodiments, a method of making a prosthesis is provided. The method can comprise providing a tissue expander and one or more samples of graft material that is sized and/or shaped to conform to at least a portion of a surface of the tissue expander, and attaching the one or more samples of graft material to the tissue expander using one of the attachment methods described above. The tissue expanders disclosed herein can be formed from a variety of suitable materials. For example, the shell of an expander may be produced from a material that is designed to prevent tissue ingrowth and/or adhesion, and which can expand when placed under force during filling. For example, in some embodiments, a tissue expander can be formed from a material that provides a smooth shell, such as silicone. In other embodiments, a tissue expander is made from a material that provides a desired surface texture, or the tissue expander is molded during formation to provide a desired surface texture.

In some embodiments, the tissue expander can be attached to the one or more samples of graft material in a medical setting or in the operating room just prior to implanting a prosthesis in a patient. In some embodiments, the tissue expander can be attached to the one or more samples of graft material prior to a surgery. In some embodiments, the tissue expander can be attached to the one or more samples of graft material prior to the surgery, so that the implantable prosthesis can be sold as a ready-to-use, off the shelf prosthesis. In some embodiments, a package or kit can comprise a prosthesis, comprising the tissue expander pre-attached to the one or more graft materials, or provided as two separate components within the package or kit. In some embodiments, the prosthesis in the kit is packaged under aseptic or sterile conditions. In certain embodiments, the kit can further comprise instructions for using the tissue expander.

In various embodiments, the graft materials are further secured to the tissue expander using biodegradable sutures, biocompatible adhesives, biocompatible glues, and/or any means of attachment known by one of skill in the art.

According to certain embodiments, methods of making a prosthesis are disclosed, comprising preparing a tissue expander, providing one or more samples of graft material sized and shaped to conform to at least a portion of a surface of a tissue expander, attaching the graft material to the shell of the tissue expander using any of the attachment methods described above to form a prosthesis, and optionally curing and/or irradiating the prosthesis.

In some embodiments the graft material comprises an acellular tissue matrix. In some embodiments the graft material comprises an acellular tissue matrix that has been treated to produce a three-dimensional porous, or sponge-like material.

In some embodiments the shell of the tissue expander and the acellular tissue matrix are cured such that the curing temperature does not reach a temperature greater than 30° C. In some embodiments the shell of the tissue expander and the acellular tissue matrix are cured such that the curing temperature does not exceed 25° C. In some embodiments the shell of the tissue expander and the extracellular tissue matrix are cured such that the curing temperature is between about 70° C. and 120° C., or between about 80° C. and 110° C., or about 100° C. In some embodiments lower or higher temperatures could be used as long as melting of the matrix proteins does not occur.

The graft materials and tissue expanders discussed herein can include one or more biocompatible materials. The biocompatible material can comprise any suitable synthetic or biologic material, such as, for example, medical grade silicone, autologous or cadaveric tissue, and/or biomatrices, such as, for example, an acellular tissue matrix ("ATM"). In some embodiments, the biocompatible material may be a flat sheet or sheet-like in form. A biocompatible material may be a single layer or may be multi-layered. In some embodiments, a biocompatible material may be a material that facilitates cell migration, repopulation, and/or revascularization. For example, in certain embodiments, a graft material can include an acellular tissue matrix ("ATM").

As used herein, ATM refers to a tissue-derived biomatrix structure that can be made from any of a wide range of collagen-containing tissues by removing all, or substantially all, viable cells and all detectable subcellular components and/or debris generated by killing cells. As used herein, an ATM lacking "substantially all viable cells" is an ATM in which the concentration of viable cells is less than 1% (e.g., less than: 0.1%; 0.01%; 0.001%; 0.0001%; 0.00001%; or 0.000001%; or any percentage in between) of the viable cells in the tissue or organ from which the ATM was derived.

For a description of exemplary ATMs that are suitable for use in the present disclosure, as well as methods of making those ATMs, see co-pending U.S. application Ser. No. 12/506,839 (published as US 2011/0022171) at paragraphs 41-73 and U.S. Provisional Application No. 61/491,787 at paragraphs 23-38 and 42-56, which are incorporated herein by reference in their entirety. Additionally, as non-limiting examples of methods of producing ATMs, mention is made of the methods described in U.S. Pat. Nos. 4,865,871; 5,366,616; and 6,933,326, and U.S. Patent Application Publication Nos. US2003/0035843 A1, and US 2005/0028228 A1, all of which are incorporated herein by reference in their entirety.

In some embodiments, the graft material can comprise STRATTICE™, a porcine dermal tissue produced by Lifecell Corporation (Branchburg, N.J.). In some embodiments, the graft material can comprise ALLODERM®, an ATM produced from human dermis by LifeCell Corporation (Branchburg, N.J.).

In some embodiments, the graft material comprises an adipose tissue matrix. In some embodiments the graft material comprises an adipose tissue matrix that has been treated to produce a three-dimensional porous, or sponge-like material. For a description of adipose tissue matrices that are suitable for use in the present disclosure, as well as methods of making adipose tissue matrices, see U.S. Provisional Application No. 61/491,787 at paragraphs 23-38 and 42-56, which is incorporated by reference in its entirety. Briefly, the process generally includes obtaining adipose tissue, mechanically processing the adipose tissue to produce small pieces, further processing the tissue to remove substantially all cellular material and/or lipids from the tissue, resuspending the tissue in a solution to form a porous matrix or sponge, and optionally cross-linking the tissue to stabilize a desired three-dimensional structure.

In certain embodiments, ready-to-use, off-the-shelf materials that are designed or further processed to conform to tissue expanders of various specifications can be used as graft materials. For a description of methods of making graft materials that are suitable for use in the present disclosure, see co-pending U.S. application Ser. No. 12/506,839 (published as US 2011/0022171). The disclosure of U.S. application Ser. No. 12/506,839 is incorporated herein by reference in its entirety.

In certain embodiments, methods of treatment are provided, comprising providing any of the prostheses described above and implanting the prosthesis into a site on a patient where a prosthesis is required (e.g., as part of a breast augmentation procedure). In certain embodiments, a prosthesis is used following a breast cancer therapy (e.g., to expand remaining native skin to receive a breast implant following a mastectomy). In other embodiments, a prosthesis is used as part of a cosmetic procedure (e.g., as part of a breast alteration procedure).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A prosthesis comprising:
   a tissue expander; and
   one or more samples of graft material releasably coupleable to the tissue expander in a manner that allows the tissue expander and the graft material to be implanted in a patient as a unitary prosthesis and in a manner that will permit the tissue expander to separate from the graft material after a period of time following implantation to allow removal of the tissue expander from an implant site while leaving the graft material within the implant site;
   wherein the prosthesis comprises one or more elongated fasteners to secure the graft material to the tissue expander; and
   wherein the graft material is configured to release from the tissue expander due to tension on the one or more elongated fasteners, the tension caused by enlargement of the tissue expander after implantation.

2. The prosthesis of claim 1, wherein the one or more samples of graft material comprise acellular tissue matrix.

3. The prosthesis of claim 1, wherein the one or more samples of graft material comprise dermal tissue matrix.

4. The prosthesis of claim 2, wherein the acellular tissue matrix comprises an adipose acellular tissue matrix.

5. The prosthesis of claim 1, wherein the one or more elongated fasteners comprise silicone.

6. The prosthesis of claim 1, wherein the one or more elongated fasteners comprise a resorbable synthetic material.

7. The prosthesis of claim 6, wherein the one or more elongated fasteners dissolve over a period of time following implantation after exposure to an aqueous implant environment such that the tissue expander is released from the graft material.

8. The prosthesis of claim 1, wherein the one or more samples of graft material comprise one or more holes, slits, or apertures through which the one or more elongated fasteners are passed to secure the graft material to the tissue expander.

9. The prosthesis of claim 1, wherein the tissue expander comprises exactly two elongated fasteners that can be passed through holes in the graft material to secure the graft material to the tissue expander.

* * * * *